(12) United States Patent
Gutierrez et al.

(10) Patent No.: US 10,098,789 B2
(45) Date of Patent: Oct. 16, 2018

(54) PREPARATION OF OCCLUSIVE DRESSINGS

(71) Applicant: Covidien LP, Mansfield, MA (US)

(72) Inventors: Carlos Gutierrez, Cumberland, RI (US); Anand Kanchagar, Auburn, MA (US)

(73) Assignee: KPR U. S. LLC, Mansfield, MA (US)

( * ) Notice: Subject to any disclaimer, the term of this patent is extended or adjusted under 35 U.S.C. 154(b) by 755 days.

(21) Appl. No.: 14/608,363

(22) Filed: Jan. 29, 2015

(65) Prior Publication Data

US 2015/0209187 A1    Jul. 30, 2015

Related U.S. Application Data

(60) Provisional application No. 61/933,561, filed on Jan. 30, 2014.

(51) Int. Cl.
| | | |
|---|---|---|
| *A61F 13/00* | (2006.01) | |
| *A61F 13/02* | (2006.01) | |
| *A61F 13/84* | (2006.01) | |
| *A61L 15/46* | (2006.01) | |

(52) U.S. Cl.
CPC .. *A61F 13/00991* (2013.01); *A61F 13/00072* (2013.01); *A61F 13/0233* (2013.01); *A61F 13/8405* (2013.01); *A61L 15/46* (2013.01); *A61L 2300/404* (2013.01); *A61L 2300/606* (2013.01); *A61L 2300/802* (2013.01)

(58) Field of Classification Search
CPC ........ A61F 13/00063; A61F 2013/0091; A61F 2013/00744; A61F 13/00012; A61F 13/00017; A61F 13/00072; A61F 13/00991; A61F 13/0233; A61F 13/8405; A61L 2300/404; A61L 15/34; A61L 2300/606; A61L 2300/802; A61L 2/232; A61L 31/16; A61L 15/46; C08L 1/02; A61M 35/00; B65B 55/08
See application file for complete search history.

(56) References Cited

U.S. PATENT DOCUMENTS

| | | | |
|---|---|---|---|
| 2,478,931 | A | 8/1949 | Masci |
| 2,764,976 | A | 10/1956 | Skiles, Jr. et al. |
| 4,984,570 | A | 1/1991 | Langen et al. |
| 6,349,289 | B1 | 2/2002 | Peterson et al. |
| 6,580,011 | B1 * | 6/2003 | Jennings-Spring ......................... A61F 13/00021 602/41 |
| 2003/0099718 | A1 * | 5/2003 | Burrell .................... A01N 59/16 424/618 |
| 2013/0150764 | A1 * | 6/2013 | Patel ................. A61F 13/00012 602/44 |
| 2013/0150765 | A1 | 6/2013 | Moghe et al. |

FOREIGN PATENT DOCUMENTS

| | | |
|---|---|---|
| CN | 1518436 A | 8/2004 |
| CN | 102431257 A | 5/2012 |

* cited by examiner

*Primary Examiner* — Mark V Stevens
(74) *Attorney, Agent, or Firm* — Nicole Creegan

(57) ABSTRACT

A method of preparing an occlusive wound dressing involves preparing a slurry of an occlusive composition with a hydrophobic compound and a bacteriostatic agent, applying the occlusive composition on a fabric to produce a coated fabric, disposing the coated fabric in packaging, adding water onto at least one of the coated fabric and the packaging, sealing the packaging containing the coated fabric, and irradiating the sealed package to sterilize and produce the occlusive wound dressing. The occlusive wound dressing has from about 60 wt % to about 75 wt % hydrophobic compound, from about 2 wt % to about 5 wt % bacteriostatic agent, from about 2 wt % to about 5 wt % water, and from about 5 wt % to about 36 wt % fabric.

14 Claims, 1 Drawing Sheet

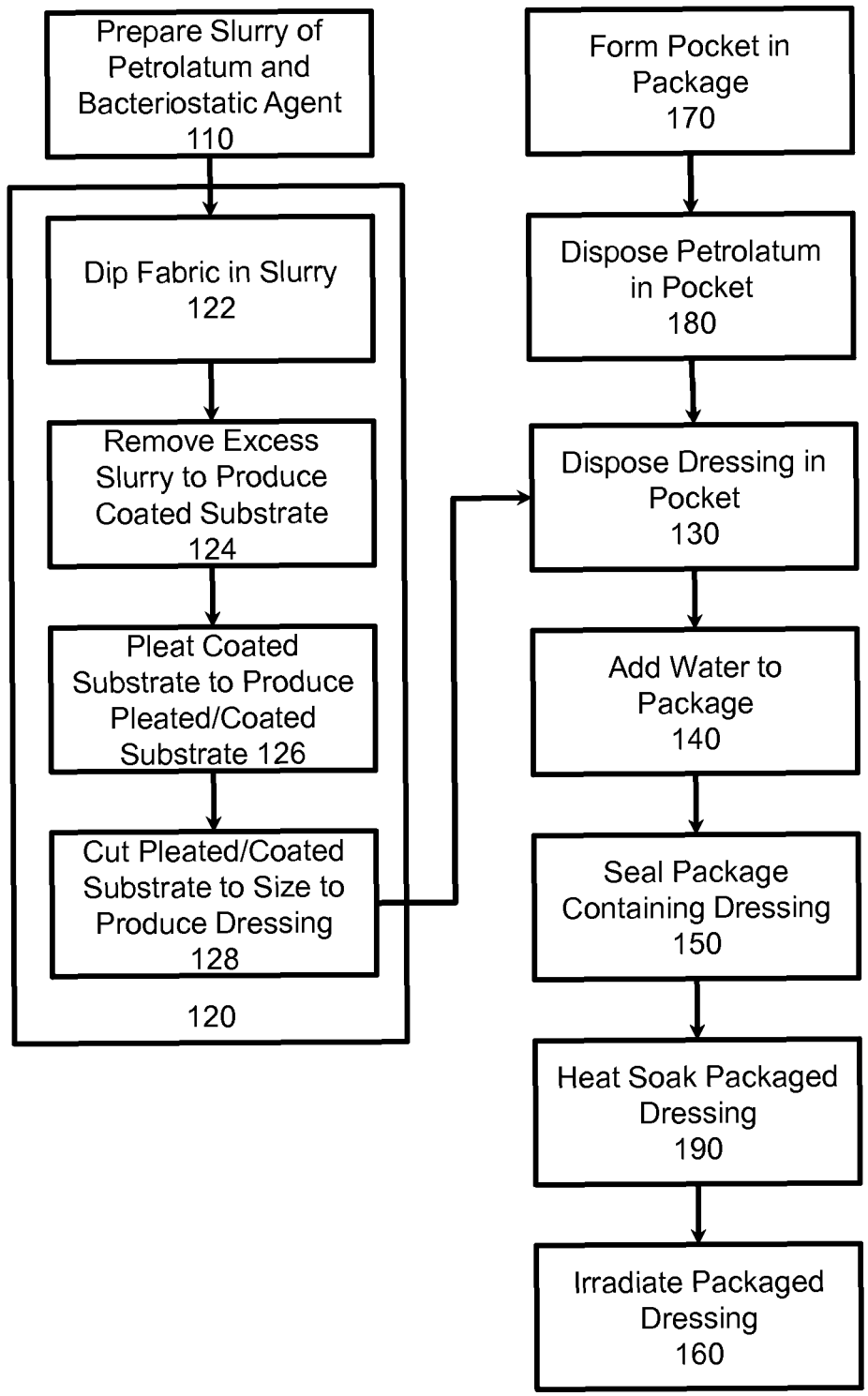

PREPARATION OF OCCLUSIVE DRESSINGS

CROSS-REFERENCE TO RELATED APPLICATION

This application is a non-provisional application of and claims the benefit under 35 U.S.C. 119 to U.S. Patent Application No. 61/933,561, titled PREPARATION OF OCCLUSIVE DRESSINGS, filed on Jan. 30, 2014, which is incorporated herein in its entirety for all purposes.

TECHNICAL FIELD

The present disclosure relates to wound dressings, and more particularly, to methods of producing occlusive wound dressings including substrates formed with fibers impregnated with petrolatum.

BACKGROUND

Wound dressings can be used to protect and to facilitate healing of wounds. Wound dressings are generally placed over a wound to protect and promote healing of the wound. In the case of exuding wounds, such as pressure sores, ulcers, and burns, it is customary to apply a dressing having an absorbent material to absorb at least a portion of the wound exudates. To promote healing, occlusive wound dressings typically do not have notable absorbent characteristics but provide an isolated, typically a water-tight and air-tight environment, to facilitate maintaining moisture at or next to the wound bed.

U.S. Pat. No. 2,478,931 discloses sterilization of packages under heat and pressure in such a manner as to minimize distortion of the package.

U.S. Pat. No. 2,764,976 discloses dressings impregnated with an oil composition.

U.S. Pat. No. 4,984,570 discloses knitted hydrophobic web wound dressings.

U.S. Patent Application Publication No. 2013/0150764 discloses non-adherent wound dressings and related methods therefor.

U.S. Patent Application Publication No. 2013/0150765 discloses antimicrobial non-adherent dressings and related methods therefor.

SUMMARY

One or more aspects of the present disclosure can be directed to a method of preparing a wound dressing. In some cases, one or more aspects of the present disclosure can be directed to a method of preparing an occlusive wound dressing. The method typically involves preparing a slurry of an occlusive composition consisting essentially of a hydrophobic compound and a bacteriostatic agent; applying a portion of the occlusive composition on a fabric comprised of at least one of cotton, polyester, rayon, cellulose acetate, and polyimide to produce a coated fabric; disposing the coated fabric on a portion of a first packaging member; introducing water on at least one of the coated fabric and the portion of the first packaging member; sealing the first packaging member to a second packaging member to produce a sealed package containing the coated fabric with the occlusive composition; irradiating the sealed package to produce the occlusive wound dressing. In some embodiments, pertinent to one or more aspects, the bacteriostatic agent can be bismuth tribromophenate. In some embodiments, the hydrophobic compound can be petrolatum. In some further embodiments, applying the portion of the occlusive composition on the fabric can involve applying the portion of the occlusive composition on fabric comprised of at least one of cotton, polyester, rayon, cellulose acetate, and polyimide, and an antibacterial agent to produce the coated fabric. The occlusive dressing can, in some cases, contain from about 60 wt % to about 75 wt % petrolatum, from about 2 wt % to about 5 wt % bismuth tribromophenate, from about 2 wt % to about 15 wt % water, and from about 5 wt % to about 36 wt % fabric. In still further embodiments, applying the portion of the occlusive composition on the fabric can involve dipping the fabric in the slurry of occlusive composition and removing excess slurry from the dipped fabric with nip rollers to produce the coated fabric. In yet further embodiments, disposing the coated fabric can involve pleating a portion of the coated fabric onto the portion of the first packaging member. The method, in some embodiments, can further involve providing a polyethylene film on at least one of a peripheral portion of the first packaging member and a peripheral portion of the second packaging member. Sealing the first packaging member to the second packaging member can involve melting at least a portion of the polyethylene film to produce the sealed package containing the coated fabric with the occlusive composition. The method can further involve, prior to disposing the coated fabric on the portion of the first packaging member, disposing a predetermined amount of the hydrophobic compound on at least one of the portion of the first packaging member and the coated fabric; and, prior to irradiating the sealed package, heat soaking the sealed package for a predetermined period. The heat soak environment can have a temperature of at least about 120° F. and the predetermined heat soak period can be at least about four hours. Irradiating the sealed package can involve exposing the sealed package to a total dose of gamma radiation in a range of from about 15 kGy to about 55 kGy. The antimicrobial agent can be one selected from the group consisting of polyhexamethylene biguanide; triclosan or 2,4,4'-trichloro-2'-hydroxydiphenyl ether; chlorhexidine and salts thereof; silver and salts or complexes thereof; polymyxin, tetracycline; aminoglycoside compounds; bacitracin; neomycin; chloramphenicol; miconazole; and combinations thereof. The method, in further embodiments, can further involve creating a pocket on the first packaging member, and wherein disposing the coated fabric on the first packaging member involves disposing at least a portion of the coated fabric in the pocket.

BRIEF DESCRIPTION OF THE DRAWING

The accompanying drawing, which is incorporated in and constitute a part of this disclosure, illustrate embodiments therein and, together therewith, serves to explain the principles of the disclosure.

FIG. 1 is a flowchart schematically illustrating exemplary steps on one or more embodiments in accordance with one or more aspects of the present disclosure.

DETAILED DESCRIPTION

One or more embodiments of the wound dressings according to the present disclosure may be used in treating burn wounds and/or other wounds where occlusive properties of the wound dressing are desirable. One or more embodiments of the wound dressings may be used as an occlusive wound dressings that provides or facilitates a moist healing environment at or about a wound bed. The wound dressings typically have enhanced non-adherent properties due to both the inclusion of a hydrophobic occlusive composition and non-adherent polymer materials. Some aspects of the present disclosure pertain to preparation of a wound dressing. In some cases, one or more steps of the method of preparation advantageously stabilize or provide a stabilized wound dressing. In some cases, one or more aspects of the disclosure can pertain to inhibiting aging or reducing the likelihood of accelerated aging of the wound dressing during manufacturing of the dressing.

Occlusive wound dressings in accordance with one or more aspects of the present disclosure typically have a substrate and an occlusive composition thereon. In some cases, the substrate can have one or more bioactive agents. In other cases, the occlusive composition can have one or more bioactive agents. In still further cases, the substrate and the occlusive composition can each have one or more bioactive agents, which can be the same or different or be variants thereof. The occlusive composition can be petrolatum and the bioactive agent can be a bacteriostatic agent. In some further examples, the bioactive agent can be an antimicrobial agent.

The method of preparing the wound dressing can involve one or more steps of providing an occlusive composition and providing a substrate upon which the occlusive composition is applied to produce a coated substrate. The method can further involve packaging the coated substrate. In some advantageous embodiments, the method further involves sterilizing the package containing the coated substrate. Sterilizing is preferably performed by irradiating the packaged, coated substrate with gamma radiation, rather than by exposure to high temperature steam. One or more further aspects of the method of preparation can advantageously involve adding a stabilizing agent. Still further aspects of the method of preparation can involve facilitating distribution of the occlusive composition on the substrate, preferably on the coated substrate when disposed in the packaging.

With reference to FIG. 1, the method of preparing the wound dressing can involve one or more steps of preparing a slurry 110 of an occlusive composition consisting essentially of a hydrophobic compound and a bacteriostatic agent, applying a portion of the occlusive composition 120 on a fabric comprised of at least one of cotton, polyester, rayon, cellulose acetate, and polyimide to produce a coated fabric, disposing the coated fabric 130 on a portion of a first packaging member, introducing water 140 on at least one of the coated fabric and the portion of the first packaging member, sealing the first packaging member to a second packaging member 150 to produce a sealed package containing the coated fabric with the occlusive composition, and irradiating the sealed package 160 to produce the occlusive wound dressing.

Applying the portion of the occlusive composition on the fabric can involve dipping the fabric 122 in the slurry of occlusive composition and removing any excess slurry 124 from the dipped fabric with nip rollers to produce the coated fabric. Disposing the coated fabric can further involve pleating a portion of the coated fabric 126 onto the portion of the first packaging member and cutting the coated fabric 128 to a predetermined size. The method can further involve providing a polyethylene film on at least one of a peripheral portion of the first packaging member and a peripheral portion of the second packaging member (not shown), and wherein sealing the first packaging member to the second packaging member can involve melting at least a portion of the polyethylene film to produce the sealed package containing the coated fabric with the occlusive composition.

The method can further involve forming a pocket on the first packaging member 170 and, in some cases, disposing a predetermined amount of the hydrophobic compound 180 on at least one of the portion of the first packaging member and the coated fabric; and, prior to irradiating the sealed package, heat soaking the sealed package 190 in an environment having a temperature of at least about 120° F. for at least about four hours.

Irradiating the sealed package can involve exposing the sealed package to a total dose of gamma radiation in a range of from about 15 kGy to about 55 kGy. Irradiation can be performed in one or more exposure periods to provide the total or target exposure dose of gamma radiation.

The antimicrobial agent can be selected from the group consisting of polyhexamethylene biguanide; triclosan or 2,4,4'-trichloro-2'-hydroxydiphenyl ether; chlorhexidine and salts thereof; silver and salts or complexes thereof; polymyxin, tetracycline; aminoglycoside compounds; bacitracin; neomycin; chloramphenicol; miconazole; and combinations thereof.

In some cases, the method can involve creating a pocket on the first packaging member and thus, disposing the coated fabric on the first packaging member can involve disposing at least a portion of the coated fabric in the pocket. Applying the portion of the occlusive composition on the fabric can involve applying the portion of the occlusive composition on fabric comprised of at least one of cotton, polyester, rayon, cellulose acetate, and polyimide, and an antibacterial agent to produce the coated fabric.

Bioactive agents such as PHMB, bismuth tribromophenate, or other medicaments, antimicrobial agents, bacteriostatic agents, hemostatic agents, tissue scaffolding agents, anti-thrombogenic agents, vasodilation agents, anesthetic agents, anti-inflammatory agents, anticancer agents, angiostatic agents, immune boosting agents, skin sealing agents, wound healing agents, and/or wound debriding agents, may be used to, for example, decrease the incidence of infection or otherwise promote healing of a wound. Any of the one or more bioactive agents may be disposed into any the fibers, yarns, substrates, and wound dressings of the disclosure by immersion thereof in a solution including one or more agents, and, optionally, drying the solvents from the immersed, coated, infused fiber, yarn, substrate or wound dressing to any desired bioactive agent concentration, for example, to a concentration that at least partially inhibits any microbial activity therein.

Introduction of the one or more bioactive agents can be performed during or after any one or more of yarns fabrication, substrates fabrication, or wound dressing fabrication, or, in some cases, after any one of bleaching and sterilizing. The bioactive agent can be in an amount ranging from about 1 wt % to about 5 wt %, based on the weight of the dressing. The at least one antimicrobial agent can include, for example, biguanides such as but not limited to polyhexamethylene biguanide (PHMB).

The at least one antimicrobial agent may be present in the substrate in an amount in a range of from about 500 ppm to about 3,500 ppm and in some cases in a range of from about 1,500 ppm to about 3,500 ppm. In some particular cases, the amount of the at least one antimicrobial agent is present in the substrate in a range of from about 500 ppm to about 1,000 ppm.

The hydrophobic compound can be white USP petrolatum commercially available from, for example, Sonneborn LLC, Parsippany, N.J., and from Calumet Specialty Products Partners, L.P., Indianapolis, Ind. For example, the hydrophobic compound can be petrolatum having a specific gravity in a range of from about 0.81 to about 0.9 at 60 C, and a melting temperature in a range of from about 35 C to about 65 C. The bacteriostatic agent typically has an effective particle diameter such that about 90 wt % of the particles have a diameter of less than about 5 μm, about 99.5 wt % of the particles have a diameter of less than about 10 μm, and/or about 99.9 wt % of the particles have a diameter of less than about 50 μm. Bismuth tribromophenate is commercially available from, for example, Omicron Quimica, SA and from Specialty Quality Products, Inc.

The occlusive dressing typically has from about 60 wt % to about 75 wt % petrolatum, from about 2 wt % to about 5 wt % bismuth tribromophenate, from about 2 wt % to about 15 wt % water, and from about 5 wt % to about 36 wt % fabric. In some cases, the occlusive dressing comprises from about 60 wt % to about 75 wt % petrolatum, from about 2 wt % to about 5 wt % bismuth tribromophenate, from about 2 wt % to about 15 wt % water, and from about 5 wt % to about 36 wt % fabric. In some cases, the occlusive dressing consists essentially of from about 60 wt % to about 75 wt % petrolatum, from about 2 wt % to about 5 wt % bismuth tribromophenate, from about 2 wt % to about 15 wt % water, and from about 5 wt % to about 36 wt % fabric. In some cases, the occlusive dressing consists of from about 60 wt % to about 75 wt % petrolatum, from about 2 wt % to about 5 wt % bismuth tribromophenate, from about 2 wt % to about 15 wt % water, and from about 5 wt % to about 36 wt % fabric.

In accordance with one or more aspects of the disclosure, the wound dressing can consist essentially of a substrate and an occlusive composition with a bacteriostatic agent. In accordance with one or more aspects of the disclosure, the wound dressing can consist essentially of a substrate, an occlusive composition with a bacteriostatic agent, and an antimicrobial agent. In some cases, the wound dressing can consist essentially of a fibrous substrate having an occlusive composition consisting essentially of petrolatum and a bacteriostatic agent disposed on the substrate. In some cases, the wound dressing can consist essentially of a fibrous substrate, an occlusive composition consisting essentially of petrolatum and a bacteriostatic agent, and an antimicrobial agent.

The substrate, in some embodiments of the disclosure, can be a woven fabric comprising first yarns and second yarns respectively interwoven in a warp direction and in a weft direction. In other cases, the substrate can be a woven fabric comprising first yarns and second yarns respectively interwoven in a weft direction and in a warp direction.

In some cases, the substrate can have a plurality of first yarns comprising cellulosic fibers. In some cases, the substrate can consist of cellulosic fibers. In still other cases, the substrate can further have a plurality of second yarns comprising non-adherent polymeric fibers. In accordance with some embodiments of the disclosure, the first yarns can have at least one of a bast fiber and another cellulosic fiber, and the second yarns can comprise non-adherent polymeric fibers. In still other cases, the substrate can consist of or consist essentially of cellulosic fibers and non-adherent polymeric fibers. In yet other cases, the substrate can consist of or consist essentially of bast fibers and cellulosic acetate fibers. For example, the wound dressing can have a substrate that consists of first yarns of at least one of a bast fiber and a cellulosic fiber, and second yarns of non-adherent polymeric fibers; and an occlusive composition with a bacteriostatic agent disposed on at least a portion the substrate. In accordance with still further embodiments of the disclosure, the wound dressing can consist essentially of first yarns consisting essentially of at least one of a bast fiber and a cellulosic fiber, and second yarns consisting essentially of non-adherent polymeric fibers; and an occlusive composition with a bacteriostatic agent on at least a portion the substrate. In accordance with yet further embodiments of the disclosure, the wound dressing can consist of first yarns consisting of at least one of a bast fiber and a cellulosic fiber, and second yarns consisting of non-adherent polymeric fibers; and an occlusive composition with a bacteriostatic agent disposed on at least a portion the substrate.

The material of the non-adherent polymeric fibers can be a polymer selected from the group consisting of polyethylene, polypropylene, polyfluoroethylene, polyfluoropropylene, polyfluoropolyethylene glycol, polytetrafluoroethylene, polyethylene terephthalate, polyethylene naphthalate, polytrimethylene terephthalate, polybutylene terephthalate, and combinations thereof. In other cases, the non-adherent fibers that can be utilized in any of the substrates disclosed herein can be comprised of sodium alginate, calcium alginate, or combinations thereof. The cellulosic material, in some embodiments of the disclosure, can comprise about 5% to about 50% by weight of the substrate. The non-adherent polymeric fibers, in some embodiments of the disclosure, can comprise about 50% to about 95% by weight of the substrate. The substrate, in accordance with one or more embodiments of the disclosure, can have at least one antimicrobial agent incorporated therein.

The at least one antimicrobial agent may be applied directly to the substrate either before or after application of the occlusive composition with a bacteriostatic agent. The one or more antimicrobial agent may be applied by spraying, solution casting, dipping, and combinations thereof. For example, U.S. Pat. No. 6,349,289 titled "Method and Manufacture of a Wound Dressing for Covering an Open Wound" describes a system and method for applying PHMB to a cellulosic bandage, which is incorporated by reference herein for all purposes.

Yarns may include any number of fibers and be dimensioned in a variety of sizes and shapes. Yarns may have a size ranging from about 25 English cotton yarn number (Ne) count to about 40 Ne count, in embodiments from about 30 Ne to about 37 Ne. Yarns may have a break factor from about 1,700 pound cotton count (lb·Ne) to about 2,500 lb·Ne, in embodiments from about 2,000 lb·Ne to about 2,200 lb·Ne.

The yarns may be braided, twisted, aligned, fused, or otherwise joined to form a variety of different wound dressing configurations. The yarns may be woven, knitted, interlaced, braided, or combinations thereof, to be formed into a substrate, such as a fabric, for a wound dressing or by other non-weaving techniques. The structure thereof will vary depending upon the assembling technique utilized to form the fabric, as well as other factors such as the type of fibers used, the tension at which the yarns are held, and the mechanical properties required of the wound dressing.

In some embodiments in accordance with some aspects of the disclosure, knitting may be utilized to form any of the various wound dressings. Knitting typically involves the intermeshing of yarns to form loops, or interloping of the yarns. In some embodiments of the disclosure, any of the various herein disclosed yarns may be warp-knitted thereby creating vertical interlocking loop chains and/or may be weft-knitted thereby creating rows of interlocking loop stitches across the wound dressing.

Any of the substrates of the present disclosure may be formed into a nonwoven substrate by a technique including any of mechanically, chemically, thermally bonding the yarns into a sheet or web in a random or systematic arrangement. For example, one or more yarns of the present disclosure may be mechanically bound by entangling the yarns to form the wound dressing by means other than knitting or weaving, such as matting, pressing, stitch-bonding, needle-punching, or otherwise interlocking the yarns to form a binderless network. Alternatively, any of the yarns may be chemically bound by an adhesive, such as a hot melt adhesive, or be thermally bound by a binder such as a powder, paste, or melt, and melting the binder on the sheet or web of yarns.

In other cases, any of the substrates of the present disclosure may be formed by spunlacing or hydroentangling fiber or yarns that have been formed by carding, airlaying, or wet-forming processes, and exposing the yarns or fibers to high speed jets of water to at least partially entangle at least a portion of the yarn or fiber, with itself and/or with other yarns or fibers. In still other cases, any of the nonwoven substrates of the present disclosure may be formed by needle-punching a precursor web of fibers or yarns, which typically have been prepared by spunbonding or by carding, and striking the yarns or fibers with barbed felting needles to at least partially interlock at least a portion of the yarn or fiber, with itself and/or with other yarns or fibers. In yet other cases, any of the nonwoven substrates of the present disclosure may be formed by extruding molten polymeric material into filaments, overlaying the molten filaments and allowing the filaments to cool and form bonds at contact points. In further cases, any of the substrates of the disclosure can be formed by meltblowing techniques which typically involve extruding molten polymeric material and drawing the extruded molten filaments with high velocity jets of air to form fine filaments that have one or more bond contact points. In yet further cases, any of the substrates of the disclosure may be formed by preparing a precursor web with thermoplastic polymeric material, which typically can be formed by any of carding, airlaying, or spunbonding, and melting at least a portion of the thermoplastic material, typically by utilizing heated calender rolls, to form bonds with other fibers. In yet further cases, any of the substrates of the present disclosure can be formed by chemically bonding at least a portion of fibers in the substrate by utilizing a chemical binder, such as latex.

Weaving may be utilized to form any of the substrates or wound dressings of the disclosure. Weaving may involve, for example, the intersection of two sets of straight yarns, warp and weft, which cross and interweave at right angles to each other, or the interlacing of two yarns at right angles to each other.

The yarns may include any number and combination of multifilament, monofilament, and/or bi-components fibers formed from cellulosic or non-adherent polymeric materials. Cellulosic material may be present in an amount from 5% to about 50% by weight of the yarns, in embodiments from about 10% to about 45% by weight of the yarns, and in further embodiments from about 15% to about 40% by weight of the yarns. The yarns may include the non-adherent polymeric material described above from 50% to about 95% by weight of the yarns, in embodiments from about 55% to about 90% by weight of the fiber, and in further embodiments from about 60% to about 80% by weight of the yarns. Yarns may be monofilament or multifilament, homogeneous or heterogeneous yarns, as described herein. The yarns may be interconnected in any manner as described herein. For example, yarns in staple form may be spun using standard spinning methodologies, such as open end spinning, ring spinning, air jet spinning, and other techniques to form any of the substrates.

The yarns, fabrics, or substrates may be scoured and bleached to meet desirable, suggested, and/or mandated standards, such as the gauze fabric standards from United States Pharmacopeia Convention. The yarns, fabrics, substrates, or wound dressings may be sterilized using standard sterility protocols to conform to suggested or mandated sterility standards. For example, the various embodiments or components thereof of the disclosure can be sterilized to conform to sterilization standards of medical devices as set forth by the International Organization for Standardization including, for example, ISO 11137 for gamma and e-beam sterilization for medical devices.

The slurry can be prepared by heating the hydrophobic compound to a temperature sufficient to melt or liquefy the hydrophobic compound, such as to a temperature in a range of from about 60 C to about 75 C, and adding and mixing the bioactive agent, such as tribromophenate, for a sufficient time to achieve homogeneity, such as for at least about 20 minutes. Preferably, the slurry is continuously or continually stirred or mixed at a slurry temperature, which can be in a range of from about 60 C to about 71 C. Application of the slurry on the substrate is preferably performed while the slurry is at the slurry temperature.

It should be understood that the wound dressings of the present disclosure are not limited to those illustrated and described herein and alternate wound dressings and components thereof may be utilized. Moreover, wound dressings of the present disclosure may be formed by layering one or more of the same or different wound dressings together to form a three-dimensional structure with any one or more desired dressing properties. For example, any of the layers of the structure can utilize any of a substrate formed of woven fibers or yarns, a substrate formed of nonwoven fibers or yarns, and a substrate formed of knitted fibers or yarns.

What is claimed:

1. A method of preparing an occlusive wound dressing, comprising:
    preparing a slurry of an occlusive composition consisting essentially of a petrolatum and bismuth tribromophenate;
    applying a portion of the occlusive composition on a fabric comprised of at least one of cotton, polyester, rayon, cellulose acetate, or polyimide to produce a coated fabric;
    disposing the coated fabric on a portion of a first packaging member;
    introducing water on at least one of the coated fabric and the portion of the first packaging member;
    sealing the first packaging member to a second packaging member to produce a sealed package containing the coated fabric with the occlusive composition; and
    irradiating the sealed package to produce the occlusive wound dressing
    wherein the occlusive wound dressing contains from about 60 wt % to about 75 wt % petrolatum, from about 2 wt % to about 5 wt % bismuth tribromophenate, from about 2 wt % to about 15 wt % water, and from about 5 wt % to about 36 wt % fabric.

2. The method of claim 1, further comprising applying an antibacterial agent to produce the coated fabric.

3. The method of claim 1, wherein applying the portion of the occlusive composition on the fabric comprises dipping the fabric in the slurry of occlusive composition and removing excess slurry from the dipped fabric to produce the coated fabric.

4. The method of claim 1, wherein disposing the coated fabric comprises pleating a portion of the coated fabric and cutting the coated fabric to a predetermined size.

5. The method of claim 1, further comprising providing a polyethylene film on at least one of a peripheral portion of the first packaging member and a peripheral portion of the second packaging member, and wherein sealing the first packaging member to the second packaging member comprises melting at least a portion of the polyethylene film to produce the sealed package containing the coated fabric with the occlusive composition.

6. The method of claim 1, further comprising, prior to disposing the coated fabric on the portion of the first packaging member, disposing a predetermined amount of the hydrophobic compound on at least one of the portion of the first packaging member and the coated fabric; and, prior to irradiating the sealed package, heat soaking the sealed package in an environment having a temperature of at least about 120° F. for at least about four hours.

7. The method of claim 1, wherein irradiating the sealed package comprises exposing the sealed package to a total dose of gamma radiation in a range of from about 15 kGy to about 55 kGy.

8. The method of claim 2, wherein the antimicrobial agent is selected from the group consisting of polyhexamethylene biguanide; 2,4,4'-trichloro-2'-hydroxydiphenyl ether; chlorhexidine and salts thereof; silver and salts or complexes thereof; polymyxin, tetracycline; aminoglycoside compounds; bacitracin; neomycin; chloramphenicol; miconazole; and combinations thereof.

9. The method of claim 1, further comprising creating a pocket on the first packaging member, and wherein disposing the coated fabric on the first packaging member comprises disposing at least a portion of the coated fabric in the pocket.

10. The method of claim 8, wherein the antimicrobial agent is present in the occlusive wound dressing in an amount from about 500 ppm to about 3,000 ppm.

11. The method of claim 8, wherein the antimicrobial agent is polyhexamethylene biguanide.

12. The method of claim 1, further comprising disposing a bioactive agent onto the fabric of the occlusive wound dressing.

13. The method of claim 12, wherein the bioactive agent is selected from the group consisting of polyhexamethylene biguanide and bismuth tribromophenate.

14. The method of claim 13, wherein the bioactive agent is bismuth tribromophenate.

* * * * *